(12) United States Patent  (10) Patent No.: US 8,647,087 B2
Daigre  (45) Date of Patent: Feb. 11, 2014

(54) COOLING SYSTEM FOR GEROTOR MOTOR

(75) Inventor: Richard Daigre, Hopkinsville, KY (US)

(73) Assignee: White Drive Products, Inc., Hopkinsville, KY (US)

( * ) Notice: Subject to any disclaimer, the term of this patent is extended or adjusted under 35 U.S.C. 154(b) by 29 days.

(21) Appl. No.: 13/561,675

(22) Filed: Jul. 30, 2012

(65) Prior Publication Data

US 2012/0285155 A1 Nov. 15, 2012

Related U.S. Application Data

(62) Division of application No. 12/474,339, filed on May 29, 2009, now Pat. No. 8,257,068.

(60) Provisional application No. 61/059,064, filed on Jun. 5, 2008.

(51) Int. Cl.
*F03C 2/00* (2006.01)
*F03C 4/00* (2006.01)
*F04C 2/00* (2006.01)

(52) U.S. Cl.
USPC ............... 418/61.3; 418/1; 418/15; 418/76; 418/132; 60/322; 60/456

(58) Field of Classification Search
USPC ........... 418/1, 15, 61.3, 76, 132–133; 60/456, 60/327, 464; 417/390
See application file for complete search history.

(56) References Cited

U.S. PATENT DOCUMENTS

| | | | |
|---|---|---|---|
| 3,045,778 A | 7/1962 | Mosbacher | |
| 3,128,707 A * | 4/1964 | Brundage | 418/15 |
| 3,233,524 A | 2/1966 | Charlson | |
| 3,240,158 A | 3/1966 | Brundage | |
| 3,396,536 A * | 8/1968 | Miller et al. | 60/456 |
| 3,863,449 A * | 2/1975 | White, Jr. | 60/456 |
| 3,964,842 A | 6/1976 | White, Jr. | |
| 4,298,318 A | 11/1981 | Tsuchiya et al. | |
| 4,411,606 A | 10/1983 | Miller | |
| 4,480,972 A | 11/1984 | Zumbusch | |
| 4,717,320 A | 1/1988 | White, Jr. | |
| 5,165,880 A | 11/1992 | White | |
| 6,457,560 B1 | 10/2002 | Evans et al. | |
| 6,699,024 B2 | 3/2004 | Dong | |
| 6,743,003 B2 | 6/2004 | Dong | |
| 6,955,045 B2 | 10/2005 | Evans | |
| 7,322,808 B2 | 1/2008 | Daigre | |
| 8,257,068 B2 * | 9/2012 | Daigre | 418/61.3 |
| 2003/0003007 A1 * | 1/2003 | Dong | 418/61.3 |
| 2007/0267068 A1 | 11/2007 | Daigre | |

* cited by examiner

*Primary Examiner* — Theresa Trieu
(74) *Attorney, Agent, or Firm* — Rankin, Hill & Clark LLP

(57) ABSTRACT

A hydraulic motor having a cooling system includes a stator, a rotor that rotates and orbits in the stator, a drive link connected to the rotor, and a housing connected with the stator. The housing includes a working fluid inlet port, a working fluid outlet port, a cooling fluid inlet port, and a cooling fluid outlet port. Each port extends through the housing and is configured to connect with a different associated external fluid line. Pressurized fluid enters the working fluid inlet port to rotate and orbit the rotor en route to the working fluid outlet port. The cooling fluid ports are isolated from the working fluid inlet port and the working fluid outlet port within the housing.

20 Claims, 4 Drawing Sheets

US 8,647,087 B2

COOLING SYSTEM FOR GEROTOR MOTOR

CROSS-REFERENCE TO RELATED APPLICATIONS

This application is a divisional of U.S. application Ser. No. 12/474,339 filed May 29, 2009, now U.S. Pat. No. 8,257,068 which is based upon and claims the benefit of provisional application No. 61/059,064, filed Jun. 5, 2008, the entirety of each is incorporated by reference.

BACKGROUND

This disclosure is directed to a hydraulic system used to propel a vehicle. More particularly, this disclosure is related to a hydraulic system that includes a gerotor motor.

Hydraulic systems that are used to propel a riding lawnmower and other small vehicles include a pump that is connected to a hydraulic motor. The pump delivers pressurized fluid, e.g., oil, to the hydraulic motor. The hydraulic motor converts the energy from the pressurized oil flow from the pump into torque and speed for transferring rotational motion to propel the riding lawnmower. As the hydraulic motor continues to work frictional forces that result from the moving components of the motor can result in high operating temperatures. Cooling the motor can increase the life of the motor as well as increase the operational efficiency.

It is known in hydraulic systems to introduce cooled oil under pressure to drive an output shaft of the hydraulic motor. In one such known hydraulic system, cooled oil is introduced into the motor and more particularly to the gerotor set in a gerotor motor. The oil exits the motor through a case drain of the motor. Hydraulic motors can also be made to include a pressurized central opening, i.e., the hydraulic motor does not include a case drain, which makes this known cooling system unsuitable for this type of motor.

SUMMARY OF THE INVENTION

A hydraulic motor having a cooling system that can overcome the aforementioned shortcomings includes a stator, a rotor that rotates and orbits in the stator, a drive link connected to the rotor, and a housing connected with the stator. The housing includes a working fluid inlet port, a working fluid outlet port, a cooling fluid inlet port, and a cooling fluid outlet port. Each port extends through the housing and is configured to connect with a different associated external fluid line. Pressurized fluid enters the working fluid inlet port to rotate and orbit the rotor en route to the working fluid outlet port. The cooling fluid ports are isolated from the working fluid inlet port and the working fluid outlet port within the housing.

An example of a hydraulic system that can overcome the aforementioned shortcomings includes a hydraulic motor, a pump, fluid lines connecting the pump to the hydraulic motor for driving and for cooling the motor, and an oil cooler connected with at least one of the fluid lines. The motor includes a housing section including a working fluid inlet port and a working fluid outlet port, a gerotor set connected with the housing section including a rotor and a stator, a drive link connected to the rotor, an output shaft connected to the drive link, and an end plate connected to the housing section closing one end of the housing section. The rotor rotates and orbits within the stator as fluid flows through the motor between the working fluid inlet port and the working fluid outlet port. The end plate includes a cooling fluid inlet port, a cooling fluid outlet port and a groove formed on an inner surface of the end plate. The groove is isolated from the working fluid inlet port and the working fluid outlet port within the motor such that cooling fluid entering the groove through the cooling fluid inlet port and exiting through the cooling fluid outlet port does not enter through the working fluid inlet port or exit through the working fluid outlet port as the cooling fluid travels through the motor.

An end plate for a gerotor motor that can operate to cool the gerotor motor includes a substantially planar inner surface, a groove extending into the end plate from the inner surface, a cooling fluid inlet port extending into the end plate from an external surface of the end plate, and a cooling fluid outlet port extending into the end plate from the external surface of the end plate. The substantially planar inner surface is configured to contact a planar surface of a component of an associated gerotor motor. The external surface of the end plate is in contact with ambient when the end plate is connected with the associated gerotor motor. The cooling fluid inlet port is in fluid communication with the groove. The cooling fluid outlet port is also in fluid communication with the groove.

An example of a hydraulic motor that reduces pressure imbalances within gerotor devices includes a housing section including an inlet port, an outlet port and a central opening, a stator connected with the housing section, a rotor that rotates and orbits in the stator when pressurized fluid is introduced into the inlet port, a drive link connected to the rotor, an output shaft connected to the drive link and disposed in the central opening, an end plate connected with the housing section, a balance plate, and a ball trapped between the balance plate and the end cover. The rotor includes a forward valving groove on a forward side of the rotor, a rear outer groove on a rear side of the rotor, a rear inner groove on the rear side of the rotor, and a passage through the rotor connecting the rear outer groove with the forward valving groove. The balance plate contacts the rear side of the rotor. The balance plate is disposed between the rotor and the end plate. The balance plate includes a shuttle cavity extending inwardly from a first planar surface of the plate, an outer passage extending inwardly from a second planar surface of the plate into the shuttle cavity, an inner passage extending inwardly from the second surface of the plate into the shuttle cavity, an outer valve seat adjacent the outer passage, and an inner valve seat adjacent the inner passage. As the rotor rotates and orbits within the stator, the rear outer groove of the rotor is swept across the balance plate so that the outer passage in the balance plate connects with the rear outer groove on the rotor and the rear inner groove on the rotor maintains fluid communication with the central opening.

DETAILED DESCRIPTION

Figure 1:
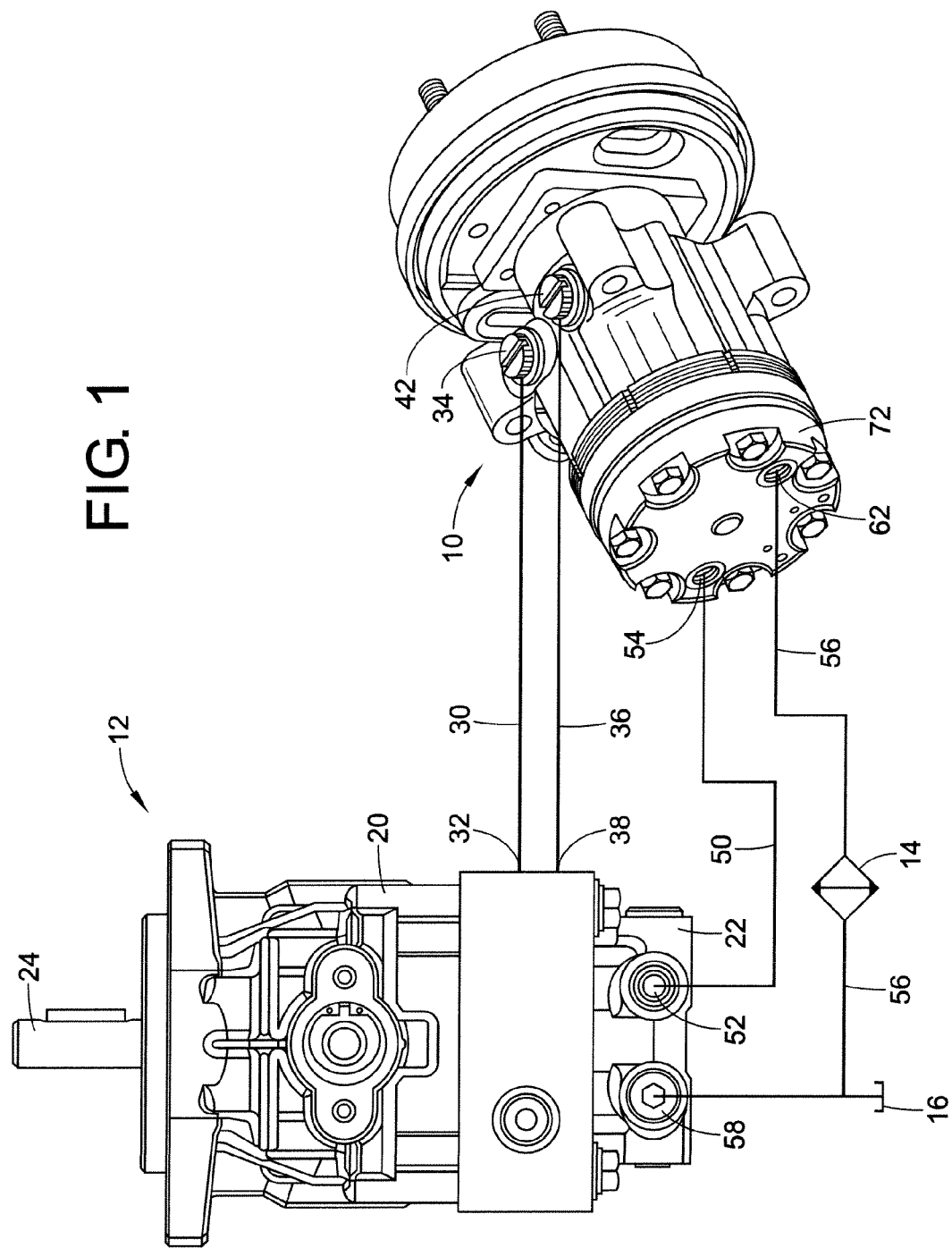
FIG. 1 schematically depicts a hydraulic system including a pump, a hydraulic motor, an oil cooler, and fluid lines connecting the pump to the hydraulic motor.

FIG. 1 schematically depicts a hydraulic system that can be used to propel a riding lawnmower. The hydraulic system in FIG. 1 can be used to propel other small land vehicles. The hydraulic system includes a hydraulic motor 10 and a pump 12 connected with the hydraulic motor via fluid lines. The fluid lines connect the pump 12 to the hydraulic motor 10 for driving and for cooling the motor. The hydraulic system further includes an oil cooler 14, e.g. a radiator, and a reservoir 16. In FIG. 1 the connection between the pump 12 and the motor 10 that propels the motor is a closed loop circuit, which can result in high operating temperatures for the motor 10. This is especially the case where the motor 10 is used to drive the wheel of a lawnmower. Accordingly, it is desirable to provide a cooling system for cooling the hydraulic motor.

The pump 12 of the hydraulic system is a conventional style pump that includes a main pump 20 and an auxiliary pump 22. The main pump 20 is a variable displacement pump and the auxiliary pump shown in FIG. 1 can be a charge pump for use with the variable displacement pump. Both the variable displacement pump 20 and the charge pump 22 in the embodiment depicted in FIG. 1 are driven by an input shaft 24, which is connected to an engine (not shown) of the lawnmower. These pumps 20 and 22 are conventional, therefore further description is unnecessary.

The fluid lines shown in FIG. 1 can include working fluid lines and cooling fluid lines. A first working fluid line 30 connects a main pump outlet 32 (depicted schematically) to a working fluid inlet port 34 (covered by a cap plug in FIG. 1) of the motor 10. A second working fluid line 36 connects a main pump inlet 38 (depicted schematically) and a working fluid outlet port 42 (shown covered by a cap plug in FIG. 1) of the hydraulic motor 10. The main pump 20, the working fluid lines 30 and 36 and the motor 10 define a closed loop circuit, which can result in high operating temperatures for the motor. Other components, e.g. a filter, can be provided in the circuit connecting the main pump 20 to the motor 10.

The fluid lines shown in FIG. 1 also include a first cooling fluid line 50 connecting an auxiliary pump outlet 52 (depicted schematically) and a cooling fluid inlet port 54. A second cooling fluid line 56 connects an auxiliary pump inlet 58 (depicted schematically) and a cooling fluid outlet port 62. The oil cooler 14 connects with at least one of the cooling fluid lines. As shown in FIG. 1, the oil cooler 14 in the depicted embodiment connects with the second cooling fluid line 56, which connects the auxiliary pump inlet 58 and the cooling outlet port 62.

As is apparent when reviewing FIG. 1, the fluid that propels the motor 10, i.e. the working fluid, is isolated from the fluid that cools the motor (other than the small amount of fluid that is delivered by the charge pump 22 to the variable displacement pump 20). The fluid that propels the motor 10 is isolated from the fluid that cools the motor within the motor itself. In other words, fluid entering the motor 10 through the cooling fluid inlet port 54 does not travel through the motor to exit through the working fluid outlet 42 of the motor. Instead, fluid entering through the cooling fluid inlet port 54 exits through the cooling fluid outlet port 62 and does not mix with fluid that is traveling through the motor to propel the motor. The internal components of the motor are shown in more detail in FIG. 2. In an alternative arrangement, fittings could be provided on the working fluid lines 30, 36. Instead of connecting the auxiliary pump outlet 52 to the cooling fluid inlet port 54, the first cooling fluid line 50 could connect with the first working fluid line 30 and the cooling fluid inlet port 54. Likewise, the second cooling fluid line 56 could connect with the second working fluid line 36 and the cooling fluid outlet port 62. In such an instance, the auxiliary pump 22 may not be provided.

Figure 2:
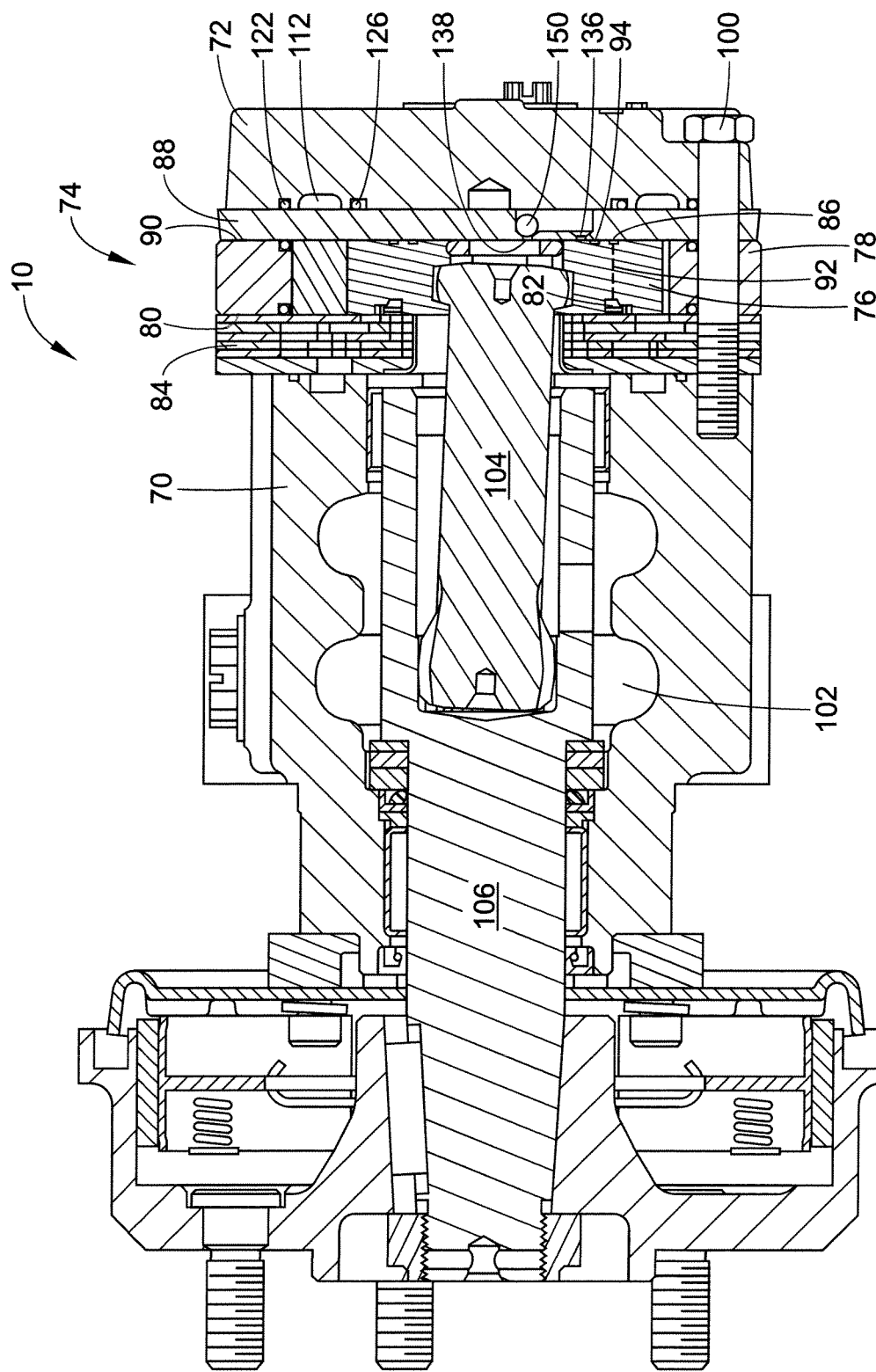
FIG. 2 is a cross-sectional view of the hydraulic motor shown in FIG. 1.
Figure 6:
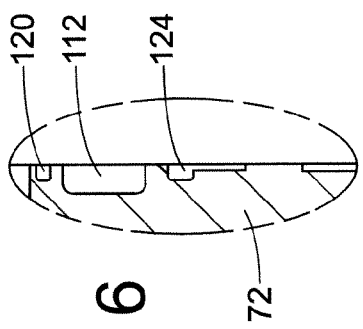
FIG. 6 is a close-up view taken from FIG. 4.
Figure 5:
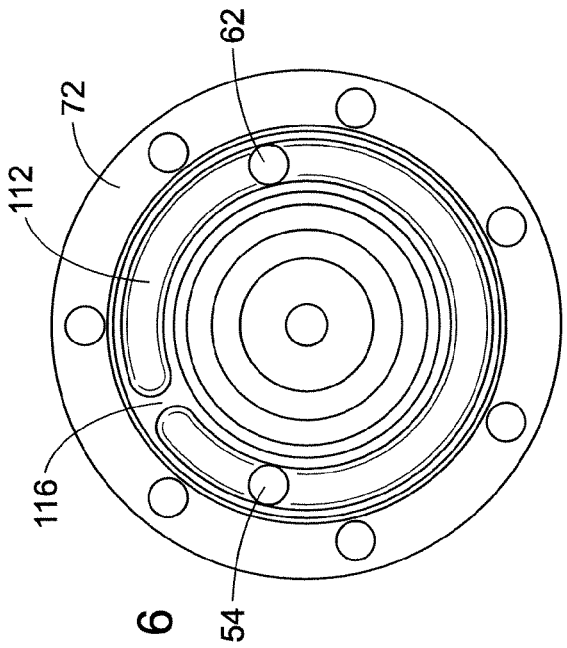
FIG. 5 is a plan view (inner side) of the end plate shown in FIG. 3.
Figure 4:
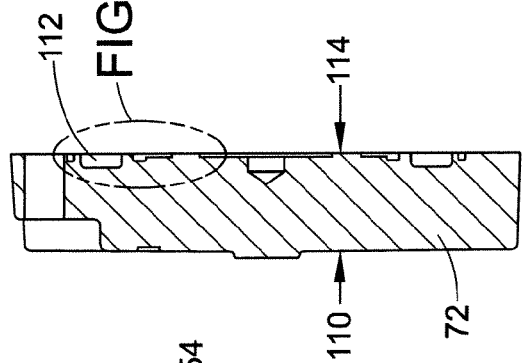
FIG. 4 is a cross-sectional view taken along line 4-4 of FIG. 3.
Figure 3:
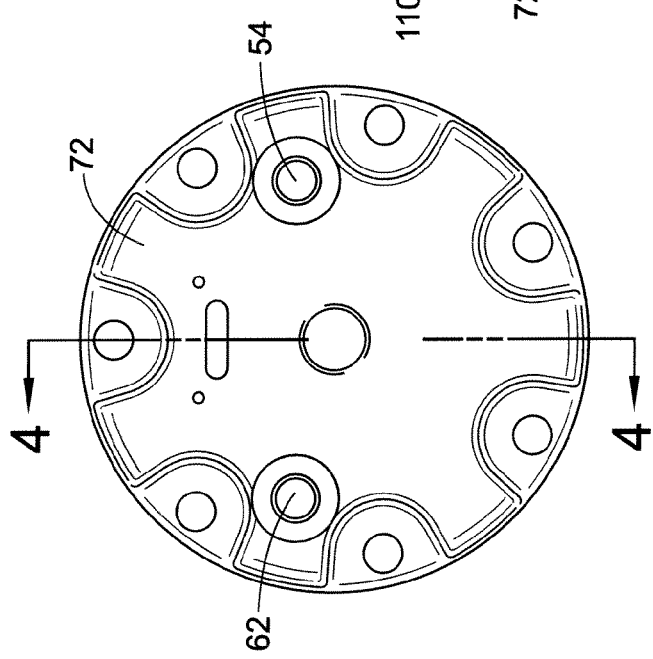
FIG. 3 is a plan view (outer side) of an end plate of the motor shown in FIG. 1.

With reference to FIG. 2, the hydraulic motor 10 includes a housing including a front housing section 70 and an end plate 72 connected with the front housing section. The housing defines the working fluid inlet port 34, the working fluid outlet port 42, the cooling fluid inlet port 54 and the cooling fluid outlet port 62, which are visible in FIG. 1. More particular to the illustrated embodiment, the working fluid inlet port 34 and the working fluid outlet port 42 are formed in the front housing section 70 and the cooling fluid inlet port 54 and the cooling fluid outlet port 62 are formed in the end plate 72. Each port 34, 42, 54 and 62 extends through the housing and is configured to connect with a different external fluid line.

The hydraulic motor 10 further includes a gerotor set 74 connected with front housing section 70 and the end plate 72. The gerotor set includes a rotor 76 and a stator 78. The rotor 76 rotates and orbits in the stator 78. The stator 78 connects with the housing.

In the embodiment depicted in FIG. 2, the rotor 76 includes a forward annular valving groove 82 on a forward planar surface 80 of the rotor adjacent a manifold 84. The forward valving groove 82 connects with an outer rear annular groove 86 disposed on a rear planar surface 90 of the rotor 76 adjacent a balance plate 88 via a passage 92 (depicted schematically). A rear inner groove 94, which is also annular, is disposed radially inwardly from the rear outer groove 86 and formed on the same rear surface 90 of the rotor 76. The functions of these grooves and passages will be provided in more detail below.

With continued reference to FIG. 2, a plurality of bolts 100 (only one visible in FIG. 2) connect the end plate 72, the balance plate 88, the gerotor set 74, and the manifold 84 to the front housing section 70. The front housing section 70 includes a central opening 102, which in the illustrated embodiment is connected with the working fluid inlet port 34 or the working fluid outlet port 42. A drive link 104 connects to the rotor 76 and is disposed within the central opening 102 of the front housing section 70. An output shaft 106 connects with the drive link 104 and is at least partially disposed within the central opening 102. The output shaft 106 depicted in FIG. 2 connects with a break assembly 108 and can also connect with the wheel (not shown) of a lawnmower. During operation of the hydraulic motor 10, the central opening 102 of the front housing section 70 can be placed under pressure, which makes the motor 10 shown in FIG. 2 unsuitable for a case drain. Accordingly, another mechanism for cooling the motor 10 is provided.

With reference to FIGS. 3-6, the end plate 72 includes the cooling fluid ports 54 and 62, which are each in communication with an annular cooling groove 112 that is milled, turned or machined into the end plate 72 from an inner planar surface 114 that abuts the balance plate 88 (see FIG. 2). The cooling fluid inlet port 54 and the cooling fluid outlet port 62 extend into the end plate 72 from an external surface 110 of the end plate 72. The external surface 110 is in contact with ambient when the end plate 72 is connected with the remainder of the motor 10. The cooling ports 54 and 62 are angularly offset from one another approximately 160° measured in a clockwise direction from the port 54 in FIG. 5 with respect to the center of the end plate 72 and the groove 112. In other words, the cooling inlet port 54 is spaced from the cooling outlet port 62 at least about a 160° around the annular groove 112. The spacing of the ports avoids a short circuit of the cooling circuit shown in FIG. 1. The cooling fluid ports 54 and 62 can be disposed closer together to one another; however, in such a configuration it may be desirable to block the annular groove 112 between the closest path between the ports to prevent a short circuit of cooling fluid. For example, a wall 116 is shown in the groove 112 blocking flow in one direction between the cooling inlet port 54 and the cooling outlet port 62.

An outer annular seal recess 120 is offset radially outwardly from the annular cooling groove 112. The outer annular seal recess 120 receives a seal 122 (FIG. 2) to isolate the cooling groove 112 from ambient. An inner annular seal groove 124 is disposed radially inwardly from the cooling groove 112 and receives a seal 126 (FIG. 2) to isolate the cooling groove 112 from the working fluid moving through the motor 10 that drives the output shaft 106 (FIG. 2). In other words, the seals isolate the cooling fluid from the working fluid in the motor. The seals 122 and 126 also isolate the fluid in the cooling groove 112 from the rotating components of the hydraulic motor. In other words, the groove 112 is isolated from the working fluid inlet port 34 and the working fluid outlet port 42 within the housing of the motor such that fluid entering the groove 112 through the cooling fluid inlet port 54 does not enter through the working fluid inlet port 34 nor exit through the working fluid outlet port 42.

The inner annular seal recess 126 is smaller than known seal recesses used to seal an end plate against a balance plate. Because of the smaller area of the inner seal recess 126, the forces on the end plate 72 and the balance plate 88 can be reduced. This increases the torque operating capability of the output shaft 106 because of less mechanical drag. Furthermore, the motor 10 does not operate as hot as a motor having a larger such recess. In the depicted embodiment, the inner annular seal recess 126 has a width measured in the radial direction of about 0.120 inches and a depth measured in the axial direction of about 0.058 inches.

With reference back to FIG. 1, the cooling circuit, which includes the charge pump 22 and the cooling fluid lines 50 and 56 connecting the charge pump to the end plate 72, cools the hydraulic motor by introducing cool oil to the end plate of the hydraulic motor. As seen in FIG. 2, the end plate 72 is adjacent the gerotor set 74 and the balance plate 88, which are typically the hottest components of the motor 10. Oil is drawn into the cooling fluid inlet port 54 and flows into the cooling groove 112. Oil exits the cooling fluid outlet port 62 en route to the radiator 14 that cools the oil prior to the oil entering back into the charge pump 22. This is in contrast to known hydraulic motor cooling systems where cooled oil is introduced under pressure to drive the output shaft of the hydraulic motor. In known hydraulic motor cooling systems, the cooled oil is introduced into the motor and exits through the motor through the case drain of the motor. Since the motor 10 shown in FIGS. 1 and 2 has a pressurized central opening, it does not include a case drain, which makes the known cooling system unsuitable for this motor. Nevertheless, the disclosed cooling system would also work with a hydraulic motor that includes a case drain.

The circuit shown in FIG. 1 separates the oil that is used to cool the motor from the oil that is used to drive the motor. The cooling passage 112 is shown in the end plate 72. The motor 10, and more particularly the housing of the motor, can include a cooling passage defined in the housing in communication with the cooling ports. For example, a cooling passage similar to the cooling passage 112 could be formed in other components of the motor, such as the balance plate 88, the stator 78, the manifold 84, and the like.

Figure 9:
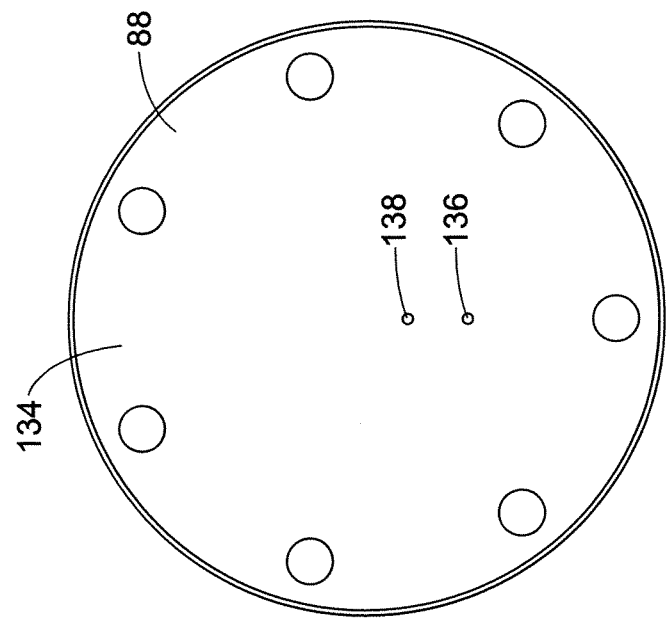
FIG. 9 is a plan view (end plate side) of the balance plate shown in FIG. 7.
Figure 8:
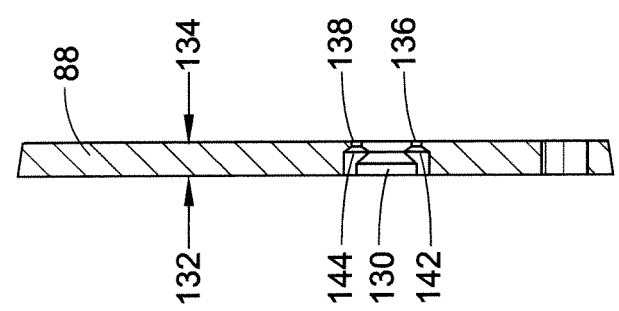
FIG. 8 is a cross-sectional view taken along line 8-8 of FIG. 7.
Figure 7:
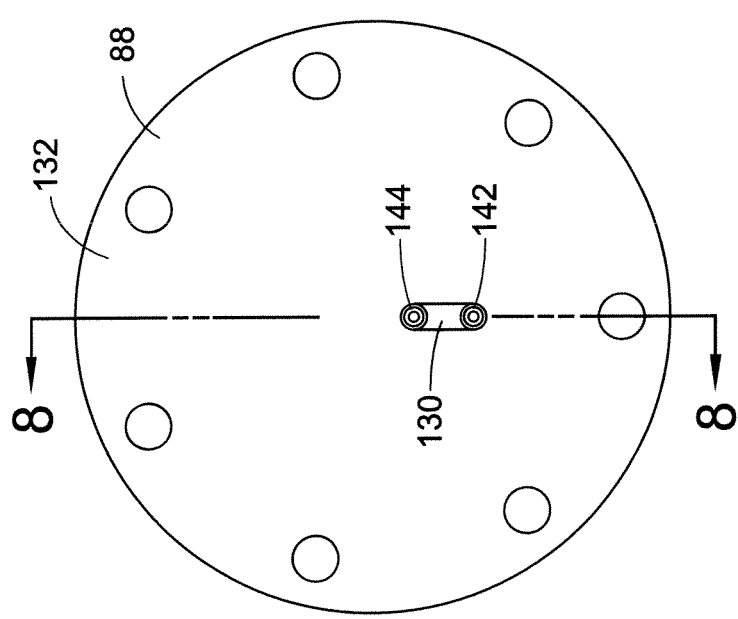
FIG. 7 is a plan view (rotor set side) of a balance plate for the motor shown in FIG. 1.

FIGS. 7-9 depict the balance plate 88 of the hydraulic motor 10. The balance plate 88 includes a shuttle cavity 130 extending axially inwardly from a planar rear surface 132 of the plate 88 toward a planar forward surface 134 of the plate. An outer passage 136 extends inwardly from the forward inner surface 134 into the shuttle cavity 130. An inner passage 138 also extends inwardly from the forward surface 134 into the cavity 130. An outer valve seat 142 is formed in the cavity 130 adjacent the outer opening 136. An inner valve seat 144 is also formed in the cavity 130 adjacent the inner opening 138. With reference back to FIG. 2, a check ball 150 is disposed in the shuttle cavity 130 and trapped between the balance plate 88 and the end cover 72.

As the rotor 76 rotates and orbits within the stator 78, the outer annular groove 86 on the rotor 76 is swept across the balance plate 88 so that the outer passage 136 in the balance plate 88 connects with the outer annular groove 86 on the rotor 76. The inner passage 138 formed in the balance plate 88 maintains fluid communication between the central opening of the rotor 76, which is in communication with the central opening 102 of the front housing section 70. Accordingly, when the central opening of the rotor 76 is under relative high pressure, the ball 150 is pushed away from the valve seat 144 (FIG. 8) and is directed toward the valve seat 142. When the central opening of the rotor is used as the outlet for the motor (relative low pressure) the ball 150 seats against the valve seat 144.

Hydraulic motors and hydraulic motor systems have been described with particularity. Alterations and modifications will occur to those upon reading and understanding the detailed description. The invention is not limited only to the embodiments described above. Instead, the invention is broadly defined by the appended claims and the equivalents thereof.

The invention claimed is:

1. A hydraulic system comprising:
    a hydraulic motor including
        a housing section including a working fluid inlet port and a working fluid outlet port;
        a gerotor set connected with the housing section including a rotor and a stator, the rotor rotating and orbiting within the stator as fluid flows through the motor between the working fluid inlet port and the working fluid outlet port;
        a drive link connected to the rotor;
        an output shaft connected to the drive link; and
        an end plate connected to the housing section closing one end of the housing section, the end plate including a cooling fluid inlet port, a cooling fluid outlet port and a groove formed on an inner surface of the end plate, the groove being isolated from the working fluid inlet port and the working fluid outlet port within the motor such that cooling fluid entering the groove through the cooling fluid inlet port and exiting through the cooling fluid outlet port does not enter through the working fluid inlet port or exit through the working fluid outlet port as the cooling fluid travels through the motor;
    a pump including a pump inlet and a pump outlet;
    fluid lines connecting the pump to the hydraulic motor for driving and for cooling the hydraulic motor; and
    an oil cooler connected with at least one of the fluid lines.

2. The hydraulic system of claim 1, wherein the oil cooler is positioned such that fluid leaving the hydraulic motor through the cooling fluid outlet port passes through the oil cooler.

3. The hydraulic system of claim 1, wherein the pump includes a main pump and an auxiliary pump, the main pump including a main pump inlet and a main pump outlet, the auxiliary pump including an auxiliary pump inlet and an auxiliary pump outlet.

4. The hydraulic system of claim 3, wherein the fluid lines include a first working fluid conduit connecting the main pump outlet and the working fluid inlet port, and a second working fluid conduit connecting the main pump inlet and the working fluid outlet port to define a closed loop circuit.

5. The hydraulic system of claim 4, wherein the fluid lines include a first cooling fluid line connecting the auxiliary pump outlet and the cooling fluid inlet port and a second cooling fluid line connecting the auxiliary pump inlet and the cooling fluid outlet port, wherein the oil cooler connects with the at least one of the cooling fluid lines.

6. The hydraulic system of claim 5, wherein the auxiliary pump mounts to the main pump and supplies fluid from a reservoir to the main pump.

7. The hydraulic system of claim 3, wherein the main pump is a variable displacement pump and the auxiliary pump is a charge pump.

8. The hydraulic system of claim 3, wherein the main pump and the auxiliary pump are driven by an engine input shaft.

9. The hydraulic system of claim 3, wherein the oil cooler is fluidly disposed between the auxiliary pump inlet and the cooling fluid outlet port.

10. A hydraulic system comprising:
   a pump including
      a main pump inlet through which working fluid is introduced into the pump;
      a main pump outlet through which the working fluid is released from the pump;
      an auxiliary pump inlet through which cooling fluid is introduced into the pump; and
      an auxiliary pump outlet through which the cooling fluid is released from the pump;
   a hydraulic motor including
      a working fluid inlet port through which the working fluid from the main pump outlet is introduced into the motor and a working fluid outlet port through which the working fluid is released from the motor to the main pump inlet;
      a gerotor set including a rotor and a stator, the rotor rotating and orbiting within the stator as the working fluid flows through the motor between the working fluid inlet port and the working fluid outlet port; and
      a cooling fluid inlet port through which the cooling fluid from the auxiliary pump outlet is introduced into the motor and a cooling fluid outlet port through which the cooling fluid is released from the motor to the auxiliary pump inlet; and
   an oil cooler fluidly disposed between the cooling fluid outlet port of the motor and the auxiliary pump inlet of the pump, wherein the motor prevents the working fluid and the cooling fluid from contacting one another while in the motor.

11. The hydraulic system of claim 10, further comprising a first working fluid line connecting the main pump outlet and the working fluid inlet port, and a second working fluid line connecting the main pump inlet and the working fluid outlet port.

12. The hydraulic system of claim 10, further comprising a first cooling fluid line connecting the auxiliary pump outlet of the pump and the cooling fluid inlet port of the motor, and a second cooling fluid line connecting the auxiliary pump inlet of the pump and the cooling fluid outlet port of the motor.

13. The hydraulic system of claim 12, wherein the oil cooler is positioned on the second cooling fluid line such that the cooling fluid leaving the motor through the cooling fluid outlet port passes through the oil cooler before passing through the auxiliary pump inlet.

14. The hydraulic system of claim 10, further comprising a reservoir that supplies cooling fluid to the pump.

15. The hydraulic system of claim 10, wherein the pump is driven by an engine input shaft.

16. The hydraulic system of claim 10, the motor further comprising an end plate including an inner surface that defines a groove formed thereon, wherein the groove is isolated from the working fluid inlet port and the working fluid outlet port within the motor such that the cooling fluid entering the groove through the cooling fluid inlet port and exiting through the cooling fluid outlet port does not enter through the working fluid inlet port or exit through the working fluid outlet port as the cooling fluid travels through the motor.

17. A method of cooling a hydraulic system, comprising:
   supplying working fluid from a main outlet of a pump to a working fluid inlet port of a motor;
   passing the working fluid from the working fluid inlet port through the motor to rotate and orbit a rotor of the motor;
   supplying cooling fluid from an outlet of the pump to a cooling fluid inlet port of the motor;
   isolating the working fluid from the cooling fluid in the motor;
   passing the cooling fluid through the motor so that the cooling fluid exits a cooling fluid outlet port of the motor; and
   passing the cooling fluid through an oil cooler.

18. The method of cooling a hydraulic system of claim 17, wherein the pump includes a main pump and an auxiliary pump, and wherein supplying working fluid further includes supplying the working fluid from the main pump.

19. The method of cooling a hydraulic system of claim 18, wherein supplying cooling fluid further includes supplying the cooling fluid from the auxiliary pump.

20. The method of cooling a hydraulic system of claim 17, wherein passing the cooling fluid through an oil cooler further includes passing the cooling fluid that has exited the cooling fluid outlet port of the motor through the oil cooler.

* * * * *